United States Patent
Marty

(10) Patent No.: US 6,933,265 B2
(45) Date of Patent: Aug. 23, 2005

(54) ALDEHYDE AS PERFUMING OR FLAVORING INGREDIENT

(75) Inventor: Maurus Marty, Gland (CH)

(73) Assignee: Firmenich SA, Geneva (CH)

(*) Notice: Subject to any disclaimer, the term of this patent is extended or adjusted under 35 U.S.C. 154(b) by 0 days.

(21) Appl. No.: 10/952,519

(22) Filed: Sep. 28, 2004

(65) Prior Publication Data

US 2005/0101498 A1 May 12, 2005

(30) Foreign Application Priority Data

Nov. 6, 2003 (WO) .................. PCT/IB03/05062

(51) Int. Cl.$^7$ .................. C11D 3/50; A61K 7/46; C07C 47/42; A23L 1/226
(52) U.S. Cl. .................. 510/106; 512/22; 568/446; 426/538
(58) Field of Search .................. 510/106; 512/22; 568/446; 426/538

(56) References Cited

U.S. PATENT DOCUMENTS

| | | | | |
|---|---|---|---|---|
| 3,929,895 A | * | 12/1975 | Hall | 568/377 |
| 4,283,561 A | * | 8/1981 | Hagen et al. | 568/446 |
| 4,416,902 A | * | 11/1983 | Mookherjee et al. | 426/3 |
| 4,594,456 A | * | 6/1986 | Schaefer-Luederssen et al. | 568/447 |
| 5,326,748 A | * | 7/1994 | Chapuis | 512/22 |
| 5,696,075 A | * | 12/1997 | Chapuis et al. | 512/6 |
| 6,376,458 B1 | * | 4/2002 | Winter | 512/26 |

FOREIGN PATENT DOCUMENTS

| | | |
|---|---|---|
| EP | 1 054 053 A2 | 11/2000 |
| JP | 50094143 A | 7/1975 |

* cited by examiner

*Primary Examiner*—John R. Hardee
(74) *Attorney, Agent, or Firm*—Winston & Strawn LLP

(57) ABSTRACT

The present invention relates to the field of perfumery or flavor. More particularly, it concerns 3-(4,4-dimethyl-1-cyclohexen-1-yl)propanal and its use as perfuming or flavoring ingredient, as well as the compositions or articles associated with said compound.

8 Claims, No Drawings

ALDEHYDE AS PERFUMING OR FLAVORING INGREDIENT

TECHNICAL FIELD

The present invention relates to the field of perfumery or flavor. More particularly, it concerns a compound of formula

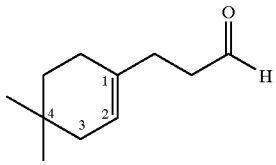

(I)

namely the 3-(4,4-dimethyl-1-cyclohexen-1-yl)propanal.

The present invention concerns the use of said compound in the perfumery or in the flavor industry as well as the compositions or articles associated with said compound.

BACKGROUND

To the best of our knowledge, the 3-(4,4-dimethyl-1-cyclohexen-1-yl)propanal is a new compound.

In the prior art it is possible to find only some structural analogues wherein only one alkyl group substitutes the carbon atom 4, in the cyclohexene ring. Some of these analogues have been described as being useful perfuming ingredients, such as the 3-(4-tert-butyl-1-cyclohexen-1-yl)propanal (in EP 1054053) or the 3-(4-isopropenyl-1-cyclohexen-1-yl)propanal (in JP 50094143).

However, to the best of our knowledge, none of the prior art documents reports or suggests that compounds having two alkyl substituents, on the carbon atom 4, may possess useful organoleptic properties, and all the less to have properties similar to that of the present compound (I).

SUMMARY OF THE INVENTION

Surprisingly, we have now established that 3-(4,4-dimethyl-1-cyclohexen-1-yl)propanal of formula

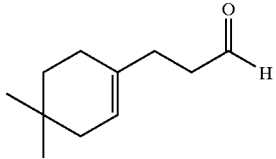

(I)

possesses useful organoleptic properties, which have been found to be particularly useful and appreciated for the preparation of perfumes or flavors.

The use of the compound (I) in the field of perfumery represents a particularly appreciated embodiment of the invention.

The flavor of the invention's compound display citrus and aldehyde C9 type notes and has also a watermelon aspect.

The fragrance of 3-(4,4-dimethyl-1-cyclohexen-1-yl)propanal is characterized by adehydic, FARENAL® (2,6,10-trimethyl-9-undecenal; origin: Symrise ag, D.), green and anisic notes as well as by a very nice floral-linden-verbena tree tonality. Moreover, a bottom note reminding of the odor of SCENTENAL® (8(9)-methoxy-tricyclo[ 5.2.1.0.(2,6)] decane-3(4)-carbaldehyde; origin: Firmenich SA, Switzerland) also characterizes the odor of compound (I). The fragrance of compound (I) is very appreciated for its linden and verbena tonality.

As mentioned above, the invention concerns also the use of the invention's compound as perfuming or flavoring ingredients. In other words it concerns a method to confer, enhance, improve or modify the odor or flavor properties of a perfuming or flavoring composition or of a perfumed or flavored article, which method comprises adding to said composition or article an effective amount of the compound of formula (I). By "use of the compound of formula (I)" it has to be understood here also the use of any composition containing compound (I) and which can be advantageously employed in perfumery or in flavors industry as active ingredients.

These compositions, which in fact can be advantageously employed as perfuming or flavoring ingredient, are also an embodiment of the present invention.

Therefore, another aspect of the present invention is a perfuming or flavoring composition comprising:
i) as perfuming or flavoring ingredient, the compound of formula (I);
ii) at least one ingredient selected from the group consisting of a perfumery carrier and a perfumery base, or at least one ingredient selected from the group consisting of a flavor carrier and a flavor base; and
iii) optionally at least one perfumery or flavor adjuvant.

DETAILED DESCRIPTION OF THE PREFERRED EMBODIMENTS

By "perfumery or flavor carrier" we mean here a material that is practically neutral from a perfumery or flavor point of view, i.e. that does not significantly alter the organoleptic properties of perfuming or flavoring ingredients. Said carrier may be a liquid or a solid.

As liquid carrier one may cite, as non-limiting examples, an emulsifying system, i.e. a solvent and a surfactant system, or a solvent commonly used in perfumery or flavors. A detailed description of the nature and type of solvents commonly used in perfumery or flavor cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. As non-limiting examples of solvents commonly used in flavors, one can cite compounds such as propylene glycol, triacetine, triethyl citrate, benzylic alcohol, ethanol, vegetal oils or terpenes.

As solid carrier one may cite, as non-limiting examples, absorbing gums or polymers, or yet encapsulating materials. Examples of such materials, for example, may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's VerlagGmbH & Co., Hamburg, 1996.

Generally speaking, by "perfumery or flavor base" we mean here a composition comprising at least one perfuming or flavoring co-ingredient.

By "perfuming or flavoring co-ingredient" it is meant here a compound, which is of current use in perfuming or flavoring preparation or composition to impart a hedonic effect. In other words such a co-ingredient, to be considered as being a perfuming or flavoring one, must be recognized by a person skilled in the art as being able to impart or modify in a positive or pleasant way the odor or taste of a composition, and not just as having an odor or taste.

The nature and type of the perfuming or flavoring co-ingredients present in the base do not warrant a more detailed description here, which in any case would not be exhaustive, the skilled person being able to select them on the basis of its general knowledge and according to intended use or application and the desired organoleptic effect. In general terms, these perfuming or flavoring co-ingredients belong to chemical classes as varied as alcohols, aldehydes, ketones, esters, ethers, acetates, nitriles, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery or flavor. It is also understood that said co-ingredients may also be compounds known to release in a controlled manner various types of perfuming or flavoring compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark ISOPAR® (origin: Exxon Chemical) or glycol ethers and glycol ether esters such as those known under the trademark DOWANOL® (origin: Dow Chemical Company).

Generally speaking, by "perfumery or flavor adjuvant" we mean here an ingredient capable of imparting additional added benefit such as a color, a particular light resistance, chemical stability and etc. A detailed description of the nature and type of adjuvant commonly used in perfuming or flavoring bases cannot be exhaustive, but it has to be mentioned that said ingredients are well known to a person skilled in the art.

An inventive composition of the compound of formula (I) and at least one perfumery or flavor carrier represents a particular embodiment of the invention as well as a perfuming or flavoring composition comprising the compound of formula (I), at least one perfumery or flavor carrier, at least one perfumery or flavor base, and optionally at least one perfumery or flavor adjuvant.

Its is also understood here that, unless otherwise indicated or described, any mixture resulting directly from a chemical synthesis, e.g. without an adequate purification, in which the compound of the invention would be involved as a starting, intermediate or end-product could not be considered as a perfuming or flavoring composition according to the invention.

The perfuming or flavoring compositions according to the invention may be a simple mixture of the various co-ingredients and solvents, or be also in the form of a biphasic system such as an emulsion or microemulsion. Alternatively, said perfuming compositions can be incorporated into a solid perfumery carrier, as defined above. In the case of flavoring bases, the latter may also be a simple mixture of flavoring ingredients or also in an encapsulated form as mentioned above. Said encapsulation is well known to a person skilled in the art, and may be performed, for instance, using techniques such as spray-drying, agglomeration or yet extrusion; or consists of a coating encapsulation, including coacervation and complex coacervation techniques.

Furthermore, the invention's compound can also be advantageously used in all the fields of modern perfumery to positively impart or modify the odor of a consumer product into which said compound (I) is added. Consequently, a perfumed article comprising:
i) as perfuming ingredient, at least one compound of formula (I) or an invention's composition; and
ii) a non-palatable consumer product base, is also an embodiment of the present invention.

For the sake of clarity, it has to be mentioned that, by "non-palatable consumer product base" we mean here a non-edible consumer product, i.e. which is not intended to be introduced in the mouth, and which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the non-palatable consumer product do not warrant a more detailed description here, which in any case would not be exhaustive, the skilled person being able to select them on the basis of its general knowledge and according to the nature and the desired effect of said product.

Examples of suitable non-palatable consumer products include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention compound, so that it may be necessary to protect the latter from premature decomposition, for example by encapsulation.

Moreover, 3-(4,4-dimethyl-1-cyclohexen-1-yl)propanal can be advantageously incorporated into a flavored article to positively impart, or modify, the taste of said article. Consequently, a flavored article comprising:
i) as flavoring ingredient, the compound of formula (I), or an invention's composition; and
ii) a foodstuff base, is also an object of the present invention.

Suitable foodstuffs, e.g. foods or beverages, include teas, beverages, such as sodas or juice, or sweets or dairy products.

For the sake of clarity, it has to be mentioned that, by "foodstuff base" we mean here an edible product, e.g. a food or a beverage. Therefore, a flavored article according to the invention comprises the functional formulation, as well as optionally additional benefit agents, corresponding to a desired edible product, e.g. a beverage, and a flavor effective amount of at least an invention's compound.

The nature and type of the constituents of the foodstuffs or beverages do not warrant a more detailed description here, which in any case would not be exhaustive, the skilled person being able to select them on the basis of its general knowledge and according to the nature of said product.

The proportions in which 3-(4,4-dimethyl-1-cyclohexen-1-yl)propanal can be incorporated into the various aforementioned articles or compositions vary within a wide range of values. These values are dependent on the nature of the article to be perfumed or flavored and on the desired organoleptic effect as well as the nature of the co-ingredients in a given base when the compound according to the invention is mixed with perfuming or flavoring co-ingredients, solvents or additives commonly used in the art.

For example, in the case of perfuming compositions, typical concentrations are in the order of 0.1% to 30% by weight, or even more, of the invention's compound based on the weight of the composition into which they are incorporated. Concentrations lower than these, such as in the order of 0.01% to 10% by weight, can be used when these compounds are incorporated into perfumed articles, percentage being relative to the weight of the article.

In the case of flavoring compositions, typical concentrations are in the order of 0.1 ppm to 1000 ppm by weight, or even more, of the compound of the invention based on the weight of the consumer product into which they are incorporated. Concentrations lower than these, such as in the order of 0.01 ppm to 200 ppm by weight, relative to the weight of the article, can be used when these compounds are incorporated into flavored articles.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with 400 MHz machine for $^1H$ and at 100 MHz for $^{13}C$, the chemical displacement δ are indicated in ppm with respect to the TMS as standard, the coupling constants J are expressed in Hz.

Example 1

Synthesis of
3-(4,4-dimethyl-1-cyclohexen-1-yl)propanal a) Synthesis of
3-(4,4-Dimethyl-cyclohex-1-enyl)-propionic Acid
Butyl Ester In a 500 ml three necked round bottom flask was charged 4,4-dimethyl-cyclohexanol (100 g, 0.78 mol) and heated up to 160° C., while adding over 4 hours tBuOOtBu (11.4 g, 0.08 mol) and ethylacrylate (39.2 g, 0.39 mol). 10 minutes after the end of the addition, the mixture was cooled to 50° C. and lights were distilled off. Then, 30% w/w aqueous NaOH (61 g) and MTBE (200 g) were added. Stirring was continued during the night at 40° C. and the aqueous phase was separated. The aqueous phase was re-extracted four times with MTBE (200 g). Afterwards, MTBE (200 g) was added to the aqueous phase, and the pH adjusted to 1 with 50% w/w aqueous $H_2SO_4$. The organic phase was washed with water and concentrated to yield 49.4 g of crude 8,8-dimethyl-1-oxa-spiro[4.5]decan-2-one (GC purity: 96.3%).

The crude 8,8-dimethyl-1-oxa-spiro[4.5]decan-2-one (40.2 g, 0.22 mol) was introduced into a 250 ml three necked round bottom flask together with butanol (23 g) and concentrated $H_2SO_4$ (0.5 g). Temperature was risen to 140° C. and during 8 hours fresh butanol (42.9 g) was introduced, while collecting a mixture of butanol/water. The reaction mixture was cooled to room temperature and toluene (66 g) and water (66 g) were added. The organic phase was washed with $NaHCO_3$ and water to yield after concentration 51.42 g of the desired compound. Flash distillation (68°–70° C., 0.2 hPa) led to 35.0 g of butylester (overall yield: 47%; GC purity: 96.0%).

IR: 2955m, 2872m, 1738s, 1460w, 1384w, 1364w, 1248w, 1164m, 1065w.

$^1$H-NMR: 5.34 (br. s, 1H); 4.06 (t, J=6.5, 2H); 2.41 (t, J=7.3, 2H); 2.27 (t, J=7.7, 2H); 1.94 (br. s, 2H); 1.76 (br. s, 2H); 1.60 (quint., J=7.1, 2H); 1.43–1.34 (m, 4H); 0.93 (t, J=7.3, 3H); 0.88 (s, 6H).

$^{13}$C-NMR: 173.7 (s); 134.6 (s); 120.7 (d); 64.2 (t); 39.2 (t); 35.6 (t); 33.1 (t); 32.7 (t); 30.7 (t); 28.5 (s); 28.1 (q); 26.0 (t); 19.2 (t); 13.7 (q).

MS: 238 (M+, 2), 164 (30), 122 (76), 109 (92), 81 (84), 41 (100).

b) Synthesis of 3-(4,4-Dimethyl-cyclohex-1-enyl)-
propan-1-ol 3-(4,4-Dimethyl-cyclohex-1-enyl)-propionic acid butyl ester (277.0 g, 1.10 mol, purity: 95%), toluene (140 g) and diethylacetate zinc complex (13.85 g, 5% w/w ester) were charged in a 2 l reactor. The pot temperature was risen to 105° C. and PMHS (Polymethylhydroxysilane, 149.0 g, 2.48 mol) was introduced over the course of 3 hours. Stirring was continued for 1 hour and then the pot temperature was decreased to 40° C. The reaction mixture was put in a dropping funnel and the 2 l reactor charged with 45% w/w aqueous KOH (403 g, 3.23 mol) and methanol (64.0 g). The pot temperature was risen to 60° C. and the reaction mixture was introduced over 30 minutes. Stirring was continued for 2 hours. The aqueous phase was separated and the organic phase washed with 5% w/w aqueous NaCl and twice with water. After concentration of the organic layer, the crude product was flash distilled (81° C., 1 hPa) to give 164.8 g of the desired alcohol (yield: 85%; GC purity: 96.2%).

IR: 3331m, 2949s, 2909s, 2870s, 1737m, 1451w, 1363w, 1164w, 1061w.

$^1$H-NMR: 5.35 (br.s, 1H); 3.63 (t, J=6.3, 2H); 2.03 (t, J=7.5, 2H); 1.94 (br. s, 2H); 1.77 (br. s, 2H); 1.68 (quint., J=7.0, 2H); 1.62 (s, OH); 1.36 (t, J=6.3, 2H); 0.89 (s, 6H).

$^{13}$C-NMR: 135.8 (s); 120.4 (d); 62.9 (t); 39.3 (t); 35.7 (t); 33.9 (t); 30.6 (t); 28.5 (s); 28.2 (q); 26.0 (t).

MS: 166 (<1); 135 (2); 124 (8); 109 (16); 95 (20); 79 (52); 68 (100).

c) Synthesis of
3-(4,4-dimethyl-1-cyclohexen-1-yl)propanal

PIPO (CAS RN: 091993-31-6; 5.04 g, 0.017 mol), NaBr (0.60 g, 0.006 mol) and $KHCO_3$ (6.40, 0.063 mol) were charged in a 2 l reactor together with water (60 g), EtOAc (250 g) and 3-(4,4-dimethyl-cyclohex-1-enyl)-propan-1-ol (100.0 g, 0.573 mol, purity: 96.5%). The pot temperature was set to 25° C. and 13% w/w aqueous NaOCl (426.8 g, 0.745 mol) was introduced over 2 hours. Stirring was continued for 1 hour and then the aqueous phase separated. Then 300 g of a 2% w/w aqueous ascorbic acid was added, and the reaction mixture was stirred for 1 hour. The aqueous phase was separated and the organic phase washed with NaHCO$_3$ and then with water. The organic phase thus obtained was concentrated and the crude product purified by a flash distillation (58°–60° C., 1 hPa) to yield 68.4 g of 3-(4,4-dimethyl-1-cyclohexen-1-yl)propanal (yield: 66%; GC purity: 92.3%).

IR: 3428w, 2950s, 2909s, 2833s, 2715w, 1727s, 1435m, 1385w, 1364m, 1190w, 1057w, 1010w, 893w, 810w.

$^1$H-NMR: 9.76 (s, 1H); 5.34 (br. s, 1H); 2.52 (td, J=7.5, J=1.7; 2H); 2.29 (t, J=7.3, 2H); 1.93 (br. s, 2H); 1.77 (br. s, 2H); 1.36 (t, J=6.3, 2H); 0.88 (s, 6H).

$^{13}$C-NMR: 202.8 (d); 134.3 (s); 121.0 (d); 42.0 (t); 39.2 (t); 35.6 (t); 29.8 (t); 28.4 (s); 28.1 (q); 26.2 (t).

Example 2

Preparation of a Perfuming Composition

A perfuming composition, having a verbena character, was prepared by admixing the following ingredients:

| Ingredient | Parts by weight |
| --- | --- |
| Benzyl acetate | 100 |
| 50%* Benjoin Sumatra essential oil | 80 |
| Bergamot essential oil | 150 |
| Citral | 50 |
| Coumarin | 50 |
| Geraniol | 350 |
| 1,3-Benzodioxole-5-carbaldehyde | 50 |
| Lemongrass | 100 |
| Muscenone[1] | 20 |
| | 950 |

*in dipropyleneglycol
[1]Methyl-cyclopentadecenone; origin: Firmenich SA, Geneva, Switzerland The addition of 50 parts by weight of 3-(4,4-dimethyl-1-cyclohexen-1-yl)propanal to the above-described perfuming composition imparted to the latter a natural floral aspect, increasing both the volume and the perceived diffusion of the fragrance. Moreover, the citrus/citral notes of the composition were accentuated, rounded, and rendered much more agreeable.

If a same amount of 3-(4-tert-butyl-1-cyclohexen-1-yl) propanal had been added, instead of the invention's compound, the perfuming composition would have acquired a much more pronounced aldehydic, green floral notes.

Example 3

Preparation of a Perfuming Composition

A perfuming composition, of the linden type, was prepared by admixing the following ingredients:

| Ingredient | Parts by weight |
| --- | --- |
| Benzyl acetate | 20 |
| Dodecyl acetate | 70 |
| 2-Phenyl-1-propanol | 190 |
| Anisic aldehyde | 10 |
| 10%* Cuminic Aldehyde | 220 |
| Cassis Base 345 B[1] | 120 |
| Cis-3-Henenol | 5 |
| 10%* Delphone[2] | 20 |
| 1,3-Benzodioxole-5-carbaldehyde[3] | 20 |
| Alpha Ionone | 20 |
| Mayol ®[4] | 240 |
| 1-(4-Methylphenyl)-1-ethanone | 5 |
| 10%* Neobutenone ®[5] | 10 |
| 10%* Methyl 2-nonynoate | 60 |
| 10%* (2E,6Z)-2,6-Nonadienal | 10 |
| Phenylethyl Alcohol | 20 |
| Methyl salicylate | 5 |
| Terpineol | 20 |
| Veloutone[6] | 5 |
| Violettyne MIP[7] | 30 |
| | 1100 |

*in dipropyleneglycol
[1]compounded perfumery base; origin: Firmenich SA, Geneva, Switzerland
[2]2-pentyl-cyclopentanone; origin: Firmenich SA, Geneva, Switzerland
[3]origin: Firmenich SA, Geneva, Switzerland
[4]cis-7-P-menthanol; origin: Firmenich SA, Geneva, Switzerland
[5]1-(5,5-dimethyl-1-cyclohexen-1-yl)-4-penten-1-one; origin: Firmenich SA, Geneva, Switzerland
[6]2,2,5-trimethyl-5-pentyl-1-cyclopentanone; origin: Firmenich SA, Geneva, Switzerland
[7]1,3-undecadien-5-yne; origin: Firmenich SA, Geneva, Switzerland The addition of 100 parts by weight of 3-(4,4-dimethyl-1-cyclohexen-1-yl)propanal to the above-described perfuming composition imparted to the latter an enhanced volume and perceived diffusion altogether with a natural floral aspect. Moreover the green linden-like freshness was greatly accentuated in a very clean manner.

The addition of an equivalent amount of 3-(4-tert-butyl-1-cyclohexen-1-yl)propanal to the above-described composition would have imparted a more aldehydic, muguet direction.

Example 4

Preparation of a Perfuming Composition

A perfuming composition for a powder detergent was prepared by admixing the following ingredients:

| Ingredient | Parts by weight |
| --- | --- |
| Linalyl acetate | 100 |
| 10%* anisaldehyde | 40 |
| Hexylcinnamic aldehyde | 300 |
| 9-Undecenal | 20 |
| Methyl benzoate | 10 |
| Benzylacetone | 230 |
| 1-Methoxy-2-methyl-3-phenylpropane[1] | 20 |
| Cetalox ®[2] | 10 |
| 10%* (2-Methoxyethyl)benzene | 405 |
| Verdyl acetate | 200 |
| Methyl 2-hydroxy-3-methylbenzoate | 10 |
| Damascone alpha[1] | 5 |
| Diphenyloxide | 10 |
| Cinnamon Leaf essential Oil | 50 |
| Habanolide ®[3] | 260 |
| 3-(1,3-Benzodioxol-5-yl)-2-methylpropanal | 100 |
| 10%* Indole | 20 |
| Iso E Super ®[4] | 120 |
| Linalool | 200 |
| Lorysia ®[5] | 350 |
| 10%* 1-(4-Methylphenyl)-1-ethanone | 60 |
| 10%* 1-Methoxy-4-methylbenzene | 50 |
| Myroxide ®[6] | 5 |
| 10%* Rose oxide | 20 |
| Phenylethyl alcohol | 600 |
| Phenylhexanol | 200 |

-continued

| Ingredient | Parts by weight |
|---|---|
| Romandolide ®[7] | 400 |
| (−)-(1S,4S,7S)-4,7,11,11-tetramethyl-tricyclo[5.4.0.0(1,3)]undecan-5-one[1] | 50 |
| 7-Tert-butyl-2H,4H-1,5-benzodioxepin-3-one | 10 |
| Tricyclo[5.2.1.0(2,6)]dec-3/4-en-8-yl isobutyrate | 100 |
| Violettyne MIP[8] | 50 |
| (1S,2S,3S)-2,6,6-trimethyl-bicyclo[3.1.1]heptane-3-spiro-2'-cyclohexen-4'-one[1] | 100 |
| Beta methylionone | 160 |
| Roselia Base 41014SA[1] | 200 |
| | 4465 |

*in dipropyleneglycol
[1] origin: Firmenich SA, Geneva, Switzerland
[2] 8,12-epoxy-13,14,15,16-tetranorlabdane; origin: Firmenich SA, Geneva, Switzerland
[3] pentadecenolide; origin: Firmenich SA, Geneva, Switzerland
[4] 1-(octahydro-2,3,8,8-tetramethyl-2-naphthalenyl)-1-ethanone; origin: International Flavors & Fragrances, USA
[5] 4-(1,1-dimethylethyl)-1-cyclohexyl acetate; origin: Firmenich SA, Geneva, Switzerland
[6] 6,7-epoxy-3,7-dimethyl-1,3-octadiene; origin: Firmenich SA, Geneva, Switzerland
[7] (1S,1'R)-[1-(3',3'-dimethyl-1'-cyclohexyl)ethoxycarbonyl]methyl propanoate; origin: Firmenich SA, Geneva, Switzerland
[8] 1,3-undecadien-5-yne; origin: Firmenich SA, Geneva, Switzerland The addition of 200 parts by weight of 3-(4,4-dimethyl-1-cyclohexen-1-yl)propanal to the above-described perfuming composition imparted to the fragrance of the latter a significantly greater presence, perceived diffusion, and a very interesting linden/verbena top note.

If a same amount of 3-(4-tert-butyl-1-cyclohexen-1-yl) propanal had been added, instead of the invention's compound, the perfuming composition would have acquired more strength. However the green, aldehydic notes, typical of said compound, would have also greatly accentuate the jasminic notes rather than the verbena notes.

What is claimed is:

1. As a compound, 3-(4,4-dimethyl-1-cyclohexen-1-yl)propanal.

2. A method to confer, enhance, improve or modify the odor or flavor properties of a perfuming or flavoring composition or of a perfumed or flavored article, which method comprises adding to said composition or article a fragrance or flavor effective amount of 3-(4,4-dimethyl-1-cyclohexen-1-yl)propanal.

3. A perfuming composition comprising:
   i) as perfuming ingredient, 3-(4,4-dimethyl-1-cyclohexen-1-yl)propanal;
   ii) at least one ingredient selected from the group consisting of a perfumery carrier and a perfumery base; and
   iii) optionally at least one perfumery adjuvant.

4. A flavoring composition comprising:
   i) as flavoring ingredient, 3-(4,4-dimethyl-1-cyclohexen-1-yl)propanal;
   ii) at least one ingredient selected from the group consisting of a flavor carrier and a flavor base; and
   iii) optionally at least one flavor adjuvant.

5. A perfumed article comprising a fragrance effective amount of 3-(4,4-dimethyl-1-cyclohexen-1-yl)propanal and a non-palatable consumer product base.

6. A perfumed article according to claim 5, wherein the non-palatable consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

7. A flavored article comprising a flavor effective amount of 3-(4,4-dimethyl-1-cyclohexen-1-yl)propanal and a foodstuff base.

8. A flavored article according to claim 7, wherein the foodstuff base is a tea, a beverage, a sweet or dairy product.

* * * * *